US010758400B2

(12) United States Patent
Cisko et al.

(10) Patent No.: US 10,758,400 B2
(45) Date of Patent: Sep. 1, 2020

(54) INFLATIONLESS RETENTION CUFF FOR FLUID COLLECTION DEVICES

(71) Applicant: Hollister Incorporated, Libertyville, IL (US)

(72) Inventors: George Cisko, Spring Grove, IL (US); Thomas Gilman, Spring Grove, IL (US); Mark Hermann, Libertyville, IL (US); Peter Visconti, Gurnee, IL (US); Noah Meade, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 194 days.

(21) Appl. No.: 15/113,192

(22) PCT Filed: Feb. 3, 2015

(86) PCT No.: PCT/US2015/014290
§ 371 (c)(1),
(2) Date: Jul. 21, 2016

(87) PCT Pub. No.: WO2015/117141
PCT Pub. Date: Aug. 6, 2015

(65) Prior Publication Data
US 2017/0000642 A1 Jan. 5, 2017

Related U.S. Application Data

(60) Provisional application No. 61/935,083, filed on Feb. 3, 2014.

(51) Int. Cl.
*A61F 5/451* (2006.01)
*A61F 5/44* (2006.01)
(52) U.S. Cl.
CPC ............... *A61F 5/451* (2013.01); *A61F 5/44* (2013.01)

(58) Field of Classification Search
CPC ......... A61F 5/451; A61F 4/445; A61J 15/003; A61J 15/0034; A61J 15/0038
See application file for complete search history.

(56) References Cited

U.S. PATENT DOCUMENTS 504,424 A 9/1893 De Pezzer
724,913 A 4/1903 Montgomery
(Continued)

FOREIGN PATENT DOCUMENTS

DE 115740 12/1900
EP 1434611 B1 6/2006
(Continued)

OTHER PUBLICATIONS

International Preliminary Report on Patentability in corresponding PCT Application No. PCT/US2015/014290 dated Aug. 9, 2016, 8 pages.
(Continued)

*Primary Examiner* — Adam Marcetich
*Assistant Examiner* — Jessica R Arble
(74) *Attorney, Agent, or Firm* — Cook Alex Ltd.

(57) ABSTRACT

A retention cuff is disclosed for retaining a fluid collection device or system in an orifice of a patient. The retention cuff has a body has a central opening and an inflationless cuff wall that includes an annular cuff wall and one or more side elements. The retention cuff is non-inflatable and has a self-deployed state or shape. The retention cuff can be coupled to a fecal collection device such that the central opening is in flow communication with a collection tube of the device and with the body of the retention device.

16 Claims, 10 Drawing Sheets

(56) References Cited

U.S. PATENT DOCUMENTS

| | | | |
|---|---|---|---|
| 3,592,197 A | 7/1971 | Cohen | |
| 3,916,896 A | 11/1975 | Ballard | |
| 4,067,335 A | 1/1978 | Silvanov | |
| 4,503,843 A | 3/1985 | Boebel | |
| 4,516,578 A | 5/1985 | Shuffield | |
| 5,356,391 A * | 10/1994 | Stewart | A61J 15/0015 128/DIG. 26 |
| 5,391,159 A | 2/1995 | Hirsch et al. | |
| 5,549,657 A * | 8/1996 | Stern | A61J 15/0015 604/246 |
| 6,030,361 A * | 2/2000 | Miyashiro | A61J 15/0015 604/523 |
| 6,168,609 B1 | 1/2001 | Kamen et al. | |
| 6,808,519 B2 | 10/2004 | Fanelli et al. | |
| 7,147,627 B2 * | 12/2006 | Kim | A61M 3/0241 604/327 |
| 7,628,775 B2 | 12/2009 | Adams et al. | |
| 7,722,583 B2 * | 5/2010 | Kim | A61M 3/0241 600/29 |
| 7,988,619 B2 | 8/2011 | Longo et al. | |
| 8,075,540 B2 * | 12/2011 | von Dyck | A61B 5/14503 600/29 |
| 8,323,255 B2 * | 12/2012 | Martino | A61M 3/0241 600/29 |
| 8,506,537 B2 | 8/2013 | Torstensen et al. | |
| 2003/0074018 A1 | 4/2003 | Torstensen et al. | |
| 2006/0030818 A1 | 2/2006 | McVey | |
| 2006/0052752 A1 * | 3/2006 | McMichael | A61J 15/0057 604/175 |
| 2009/0216206 A1 * | 8/2009 | Nishtala | A61M 39/10 604/327 |
| 2009/0326490 A1 * | 12/2009 | McMichael | A61F 5/451 604/328 |
| 2010/0185155 A1 * | 7/2010 | McMichael | A61J 15/0038 604/175 |

FOREIGN PATENT DOCUMENTS

| | | |
|---|---|---|
| GB | 2516429 A | 1/2015 |
| WO | 2009015152 A1 | 1/2009 |
| WO | 2010089651 A2 | 8/2010 |

OTHER PUBLICATIONS

International Search Report and Written Opinion in corresponding PCT Application No. PCT/US2015/014290, dated Jun. 16, 2015, 6 pages.

EPO Office Action dated Dec. 6, 2018 for Application No. EP15707196.0.

Australian Office Action dated Sep. 18, 2018 for Application No. 2015210632.

* cited by examiner

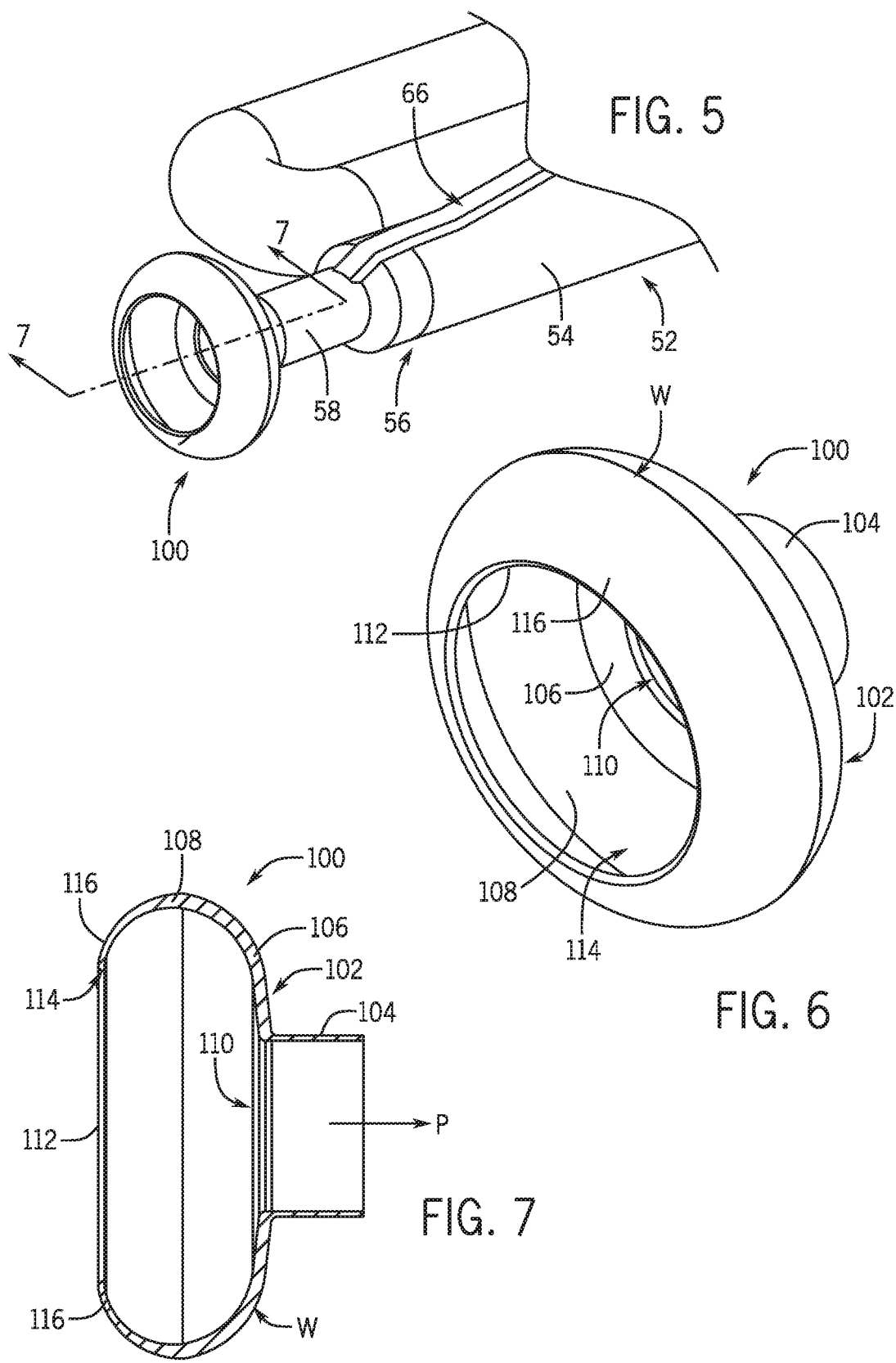

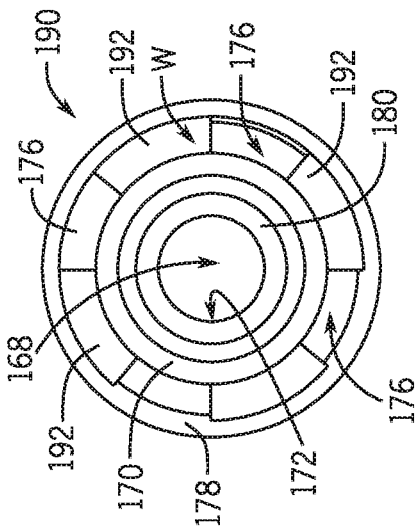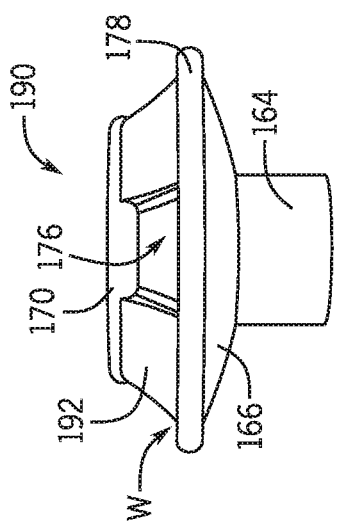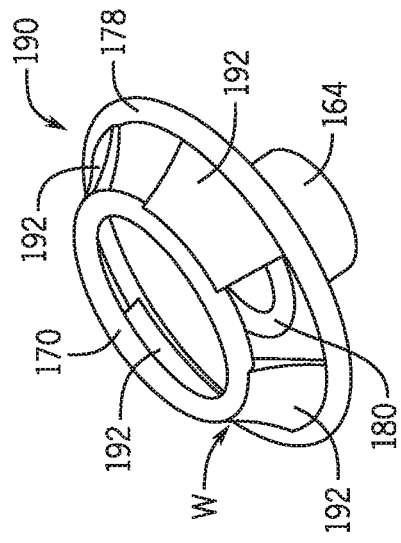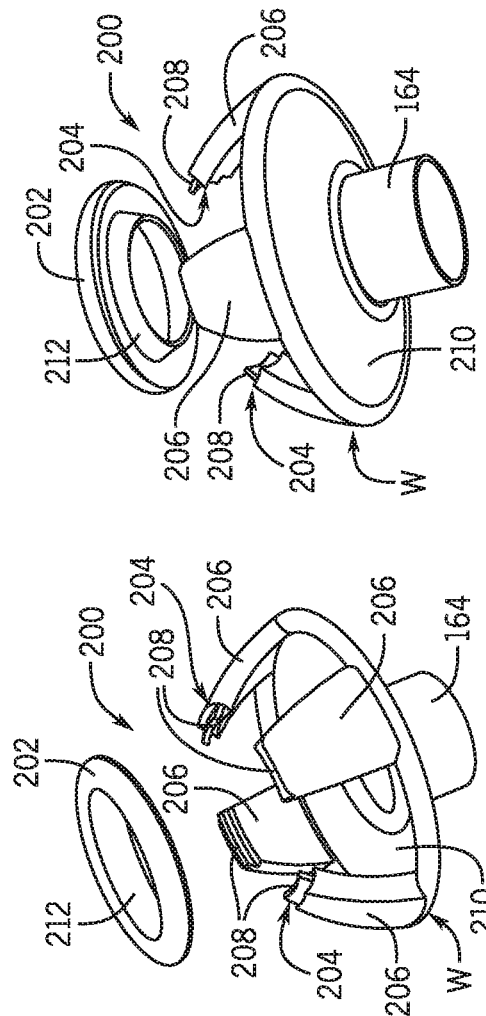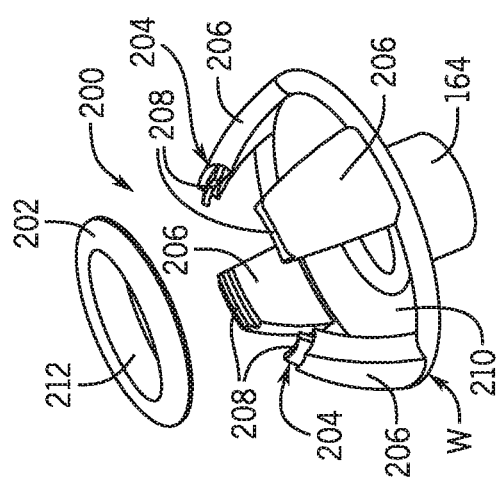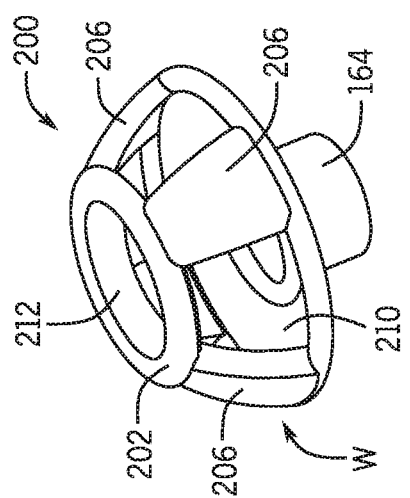

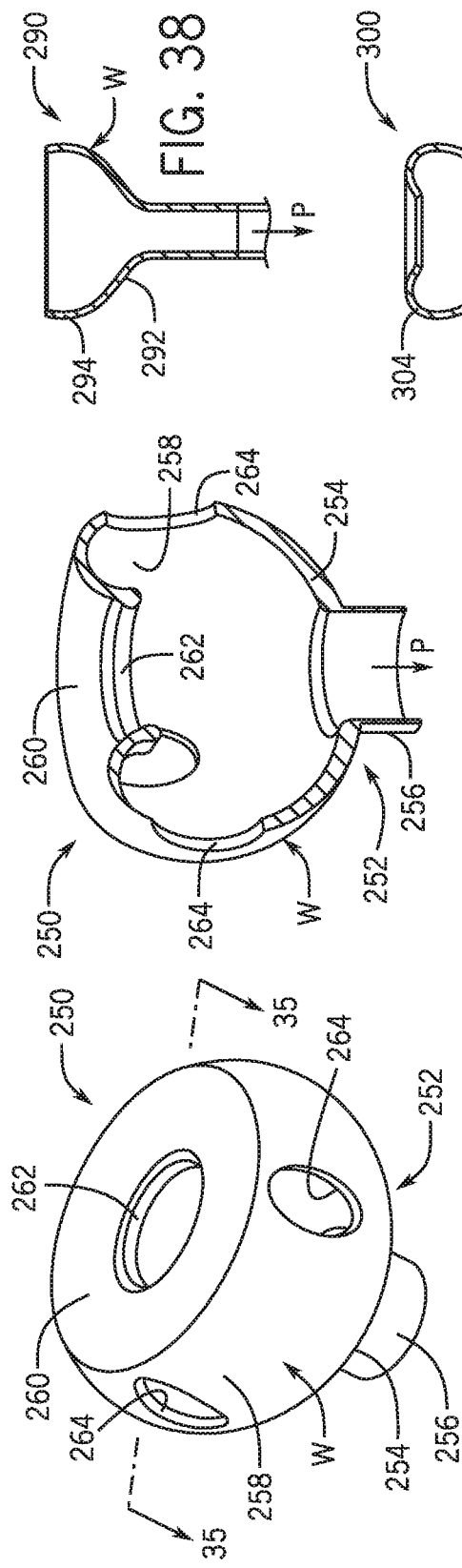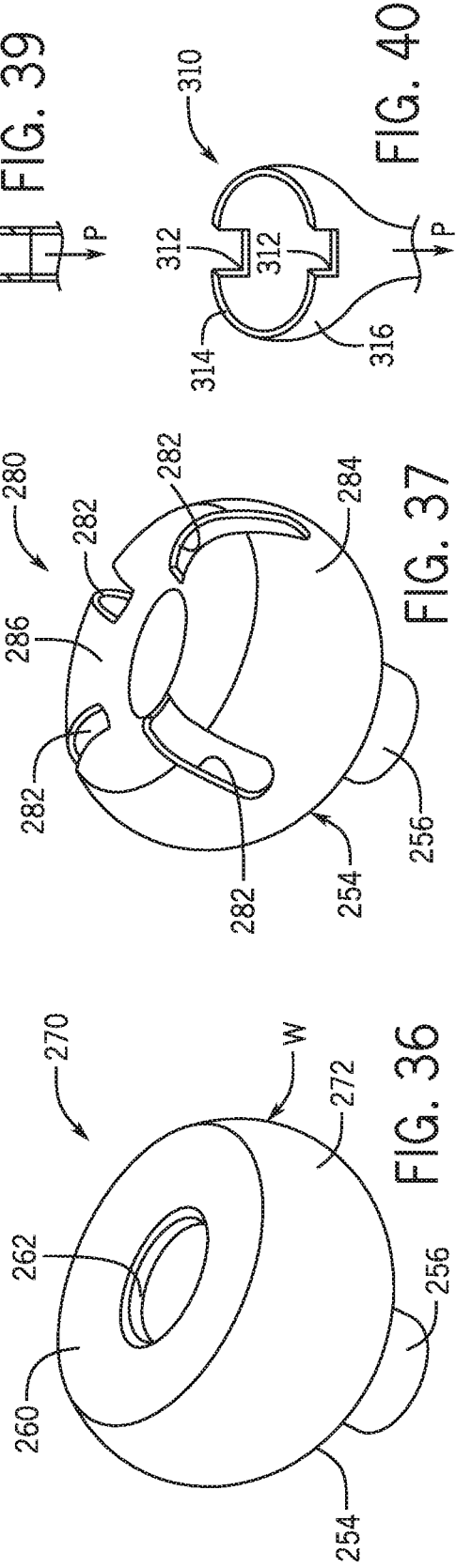

INFLATIONLESS RETENTION CUFF FOR FLUID COLLECTION DEVICES

RELATED APPLICATION DATA

This patent is related to and claims priority benefit of U.S. provisional application Ser. No. 61/935,083 filed on Feb. 3, 2014 and entitled "Inflationless Retention Cuff for Bowel Management System." The entire contents of this prior filed provisional application are hereby incorporated herein by reference.

BACKGROUND

1. Field of the Disclosure

The present disclosure is generally directed to retention cuffs for medical fluid collection systems and devices, and more particularly to an inflationless retention cuff for a fluid collection tube, drainage tube, bowel catheter, or the like.

2. Description of Related Art

Commercially known drainage tubes for bowel management systems and devices are known to include a generally spheroidal or spherical retention cuff or balloon at the free, patient insertion end of the tube. During use, these retention cuffs are inflatable with air, water, saline solution, or the like. Filling or inflating the inflatable cuffs requires an extra step for medical personnel to properly install the drainage lumen on a patient. The cuff must also be deflated when removing the device from the patient, thus requiring another additional step. Such products also require additional materials and equipment including a syringe and the fluid to fill the balloon or cuff. An inflation lumen is also required to deliver the fluid to the balloon. The lumen typically also has an undesirable hard connector for connection of the syringe in order to fill the retention cuff.

These existing retention cuffs are also known to leak. Such retention cuffs are typically filled or inflated to a turgid or substantially fixed shape. These prior known balloon shapes are not designed to conform specifically to the human anatomy to the extent that the device can account for the "anorectal angle" of a patient. In other words, no known devices take into account, in their design configuration, the angle created by the kink in the lower gastro-intestinal tract that prevents incontinence in an upright walking person.

Also, as a patient's anal muscles tense and relax, and as the patient moves, the shape, configuration, and contour of the patient's anal canal, rectal vault, and/or rectal ampulla changes. The typical spheroidal retention cuff does not hold a tight seal during all such conditions, particularly when inflated to a turgid condition. Thus, the cuff can leak and the catheter can migrate in and out, and can result in unintended, and even frequent, expulsion of the catheter from the patient's anus.

Further, over-inflating this type of retention cuff with additional water or fluid is a common problem whether accidental or as a troubleshooting technique to help reduce leaking and to aid in retention of the catheter, i.e., to help reduce the frequency of catheter expulsion from the patient's anus. However, adding more fluid to the retention cuff often does not reduce leaking or expulsion frequency but can cause discomfort and even injury to the patient. Others have tried to solve these problems by adding less, not more, liquid to the conventional retention cuff. This has not been shown to aid in cuff retention or in preventing leaks. Still others have tried to alleviate this problem by adding air instead of liquid to the retention cuff, but to the same result. These solutions have proven less than adequate in solving the foregoing problems.

Another problem with these inflatable retention cuffs is that the balloons are relatively difficult to manufacture. Also, the thin material required to manufacture the walls of the balloon shape of the cuff can be quite expensive. These factors can add significant cost to bowel management systems and devices. Further, the thin material required to form such balloons can be easily damaged or punctured, which can result in the device not being suitable for use and thus needing to be discarded and replaced.

Bowel catheters and drainage tubes provide a conduit for control of fecal material exiting a patient's body. These devices keep fecal material away from the skin and separate from the external environment and instead direct the material to a collection bag. The conduit is held in place inside the rectum by the retention cuff that is inflated after it is inserted into the rectum. The retention cuff typically includes a very flexible inflation balloon like element that is attached to an annulus on one end of the tube. The opening in the annulus is the beginning of the conduit for fecal material. In some product forms, the annulus is simply the distal end of the conduit tubing.

One advantage is achieved by having a separate annulus in the area of balloon attachment, where this annulus is stiffer than the conduit tubing. Such a construction provides more resistance to spontaneous expulsion of the bowel catheter from the rectum. This type of spontaneous expulsion is quite undesirable. Also, and perhaps even more importantly, such a construction provides a level of collapse resistance of the cuff, allowing the cuff and annulus to maintain patency. One disadvantage of providing a stiff annulus, however, is that depending on the design, the edges of the annulus can be points of stress concentration in the device. These points or edges can potentially cause irritation or damage to the patient's body where these edges come into contact with the rectal wall.

Another problem with these types of retention cuffs is that in part, due to the anorectal angle and pressure applied by the rectal wall, the rectal wall can partially or completely occlude the opening of the annulus during use of the product. Heretofore, there has been no elegant or adequate solution to this problem. Further, the balloon retention cuffs have only one fluid flow path into the drainage lumen or tube. That path is an axial flow path that is parallel to the axis of the tube or drainage lumen. Occlusion of the opening in the cuff to the flow path can thus significantly reduce or prevent flow of fecal matter into the drainage lumen or tube. These types of known drainage lumens and balloons are made of very soft and flexible material, which can further result in occlusion of the flow path during use.

SUMMARY

In one example according to the teachings of the present disclosure, a fecal collection device has a collection tube and a retention cuff coupled to one end of the collection tube. The retention cuff has a non-inflatable body including a neck portion coupled to the one end of the tube, a central opening through the neck portion in axial flow communication with the collection tube and the body, and an inflationless cuff wall. The inflationless cuff wall has at least an annular cuff wall extending radially outward from the neck portion and has at least a portion that is angled in an axial direction away from the collection tube. The inflationless cuff wall surrounds the central opening and has an undeformed shape configured to direct collected fecal matter to the collection tube through the central opening.

In one example, the annular cuff wall can have a generally frusto-conical shape or a funnel shape.

In one example, the annular cuff wall can define at least part of the portion that is angled in the axial direction.

In one example, one or more side elements of the inflationless cuff wall can define at least part of the portion that is angled in the axial direction.

In one example, the one or more side elements can include a side wall or a plurality of spars or both.

In one example, the inflationless cuff wall can have a generally curved bowl shape or curved dish shape.

In one example, the annular cuff wall can have a thickness that varies in a radial direction.

In one example, the inflationless cuff wall can include a side wall that can be formed as a continuation of the annular cuff wall. At least part of the side wall can extend in the axial direction further away from the collection tube and can define an axial opening into the body.

In one example, the inflationless cuff wall can include a side wall that can be formed as a contiguous continuation of the annular cuff wall. At least part of the side wall can extend axially away from the one end of the collection tube and can define an axial opening into the body. The side wall can have one or more radial flow pathways formed laterally into the body.

In one example, the inflationless cuff wall can include one or more radial flow pathways that can be defined by one or more openings, sub-channels, or slots formed through a side wall of the inflationless cuff wall.

In one example, the retention cuff can include a plurality of spars extending in an axial direction away from the one end of the collection tube. The plurality of spars can form one or more lateral flow pathways therebetween and into the cuff body.

In one example, the retention cuff can include a plurality of spars that extend from a portion of the annular cuff wall.

In one example, the retention cuff can include a plurality of spars that extend from a perimeter free edge of the annular cuff wall.

In one example, the retention cuff can have a central core with one or more spars forming one or more lateral or radial flow pathways into the cuff body.

In one example, the retention cuff can include a central core that can be a part of the body.

In one example, the retention cuff can include a central core that is positioned axially aligned with the central opening and is a part of the body positioned radially inward of a perimeter edge of the annular cuff wall.

In one example, at least the inflationless cuff wall can be formed of a resilient flexible material that can be physically deformed from the undeformed shape by an applied force upon the inflationless cuff wall and that will return to the undeformed shape when not subjected to the applied force.

In one example according to the teachings of the present invention, a retention cuff is disclosed and configured to retain a fluid collection device or system in an orifice of a patient. The retention cuff has a central opening and a body with an inflationless cuff wall that includes an annular cuff wall and one or more side elements. The retention cuff is non-inflatable and has a self-deployed state or shape.

In one example, the one or more side elements can include a side wall extending from and connected to the annular cuff wall.

In one example, the one or more side elements can include a plurality of spars connected to and extending in an axial direction from the annular cuff wall.

In one example, the retention cuff can include one or more lateral or radial flow path openings through or between the one or more side elements.

In one example, the one or more side elements can include a plurality of spars that can be connected to and extend in an axial direction from the annular cuff wall Distal ends of the one or more spars can be joined to one another at a blunt nose axially aligned with but spaced from the central opening.

In one example, the inflationless cuff wall can have a curved bowl or dish shape.

In one example, the one or more side elements can be one or more spars that can be joined to the annular cuff wall radially inward of a perimeter outer edge of the annular cuff wall.

BRIEF DESCRIPTION OF THE DRAWINGS

Objects, features, and advantages of the present invention will become apparent upon reading the following description in conjunction with the drawing figures, in which:

FIG. 5 shows a perspective view of a portion of another example of a fecal collection device constructed in accordance with the teachings of the present invention.

FIG. 6 shows an enlarged perspective view of an inflationless retention cuff portion of the device shown in FIG. 5 and constructed in accordance with the teachings of the present invention.

FIG. 7 shows a cross-section taken along line 7-7 of the retention cuff portion shown in FIG. 5.

FIG. 21 shows a perspective view of another example of an inflationless retention cuff portion of a device such as that shown in FIG. 17 and constructed in accordance with the teachings of the present invention.

FIG. 22 shows a side view of the retention cuff portion of FIG. 21.

FIG. 23 shows a top view of the retention cuff portion of FIG. 21.

FIG. 24 shows a perspective view of another example of an inflationless retention cuff portion of a device such as that shown in FIG. 17 and constructed in accordance with the teachings of the present invention.

FIG. 25 shows an exploded perspective view of the retention cuff of FIG. 24.

FIG. 26 shows an alternate perspective view of the retention cuff of FIG. 25.

FIG. 34 shows an enlarged perspective view of another example of an inflationless retention cuff portion of a device such as that shown in FIG. 1 and constructed in accordance with the teachings of the present invention.

FIG. 35 shows a cross-section taken along line 35-35 of the retention cuff portion of FIG. 34.

FIGS. 36 and 37 show enlarged perspective views of further examples of inflationless retention cuff portions of devices such as that shown in FIG. 1 and constructed in accordance with the teachings of the present invention.

FIGS. 38 and 39 show additional cross-section views of further examples of inflationless retention cuff portions of devices such as that shown in FIG. 1 and constructed in accordance with the teachings of the present invention.

FIG. 40 shows a perspective view of another example of an inflationless retention cuff of a device such as that shown in FIG. 1 and constructed in accordance with the teachings of the present invention.

DETAILED DESCRIPTION OF THE DISCLOSURE

The present disclosure describes various embodiments of a retention cuff that is not inflatable. The disclosed retention cuffs reduce the number of steps required to install and remove the bowel management system or device from a patient because the cuff need not be inflated after insertion or deflated before removal. The disclosed retention cuffs thus alleviate the over-inflation problems noted above with known catheter retention cuff balloons. Prior known balloons are turgid even when properly filled, which also causes problems as noted above. The present disclosure describes retention cuffs that can have a relatively symmetrical shape or that can have an irregular shape. The disclosed retention cuffs can have a solid side wall or a side wall with lateral flow sub-channels, pathways, openings, slots, or the like. The disclosed inflationless retention cuffs can have an annular cuff wall and a neck portion that can act as a cushion between edges of the drainage tube or bowel catheter and the rectal tissue of a patient, particularly when inserting the tube or catheter into the patient's anal canal. The disclosed retention cuffs may also have a configuration that, even when the axial opening into the collection tube might be partially occluded, a path for fluid flow into the transphincter section or the drainage tube is maintained through at least part of the inflationless retention cuff. The disclosed retention cuff examples can adhere or cling to the walls and floor of the rectal vault by resiliency and flexibility of at least an annular cuff wall portion of the cuff surrounding the central opening. This prevents leaks by maintaining a seal therebetween, even with the action of contracting and relaxing of the muscles that control defecation and patient movement. The disclosed inflationless retention cuff embodiments solve or improve upon one or more of the above-noted and/or other problems and disadvantages with prior known inflatable retention cuffs and rectal catheter systems.

Figure 1:
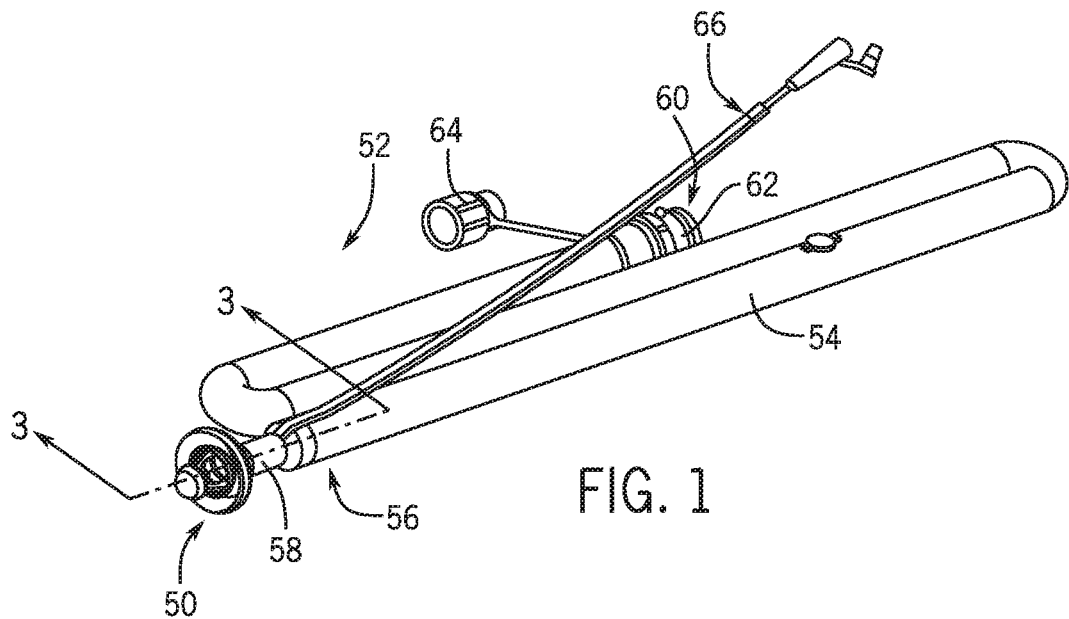
FIG. 1 shows a perspective view of one example of a fecal collection device constructed in accordance with the teachings of the present invention.
Figure 2:
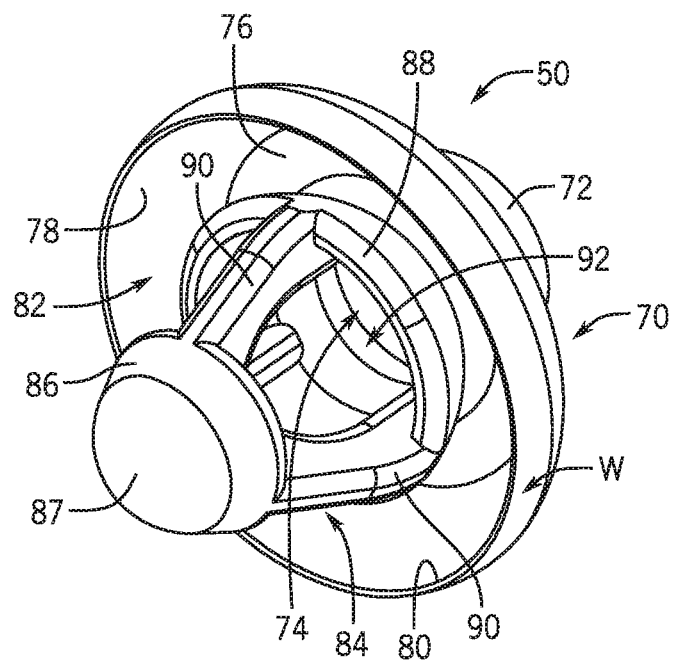
FIG. 2 shows an enlarged perspective view of an inflationless retention cuff portion of the device shown in FIG. 1 and constructed in accordance with the teachings of the present invention.
Figure 3:
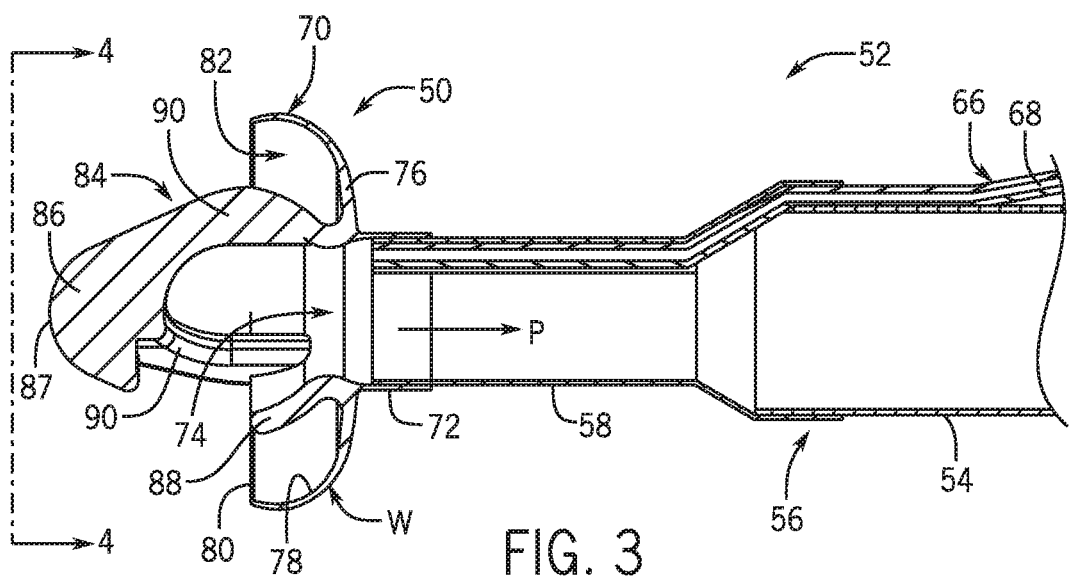
FIG. 3 shows a cross-section taken along line 3-3 of the device shown in FIG. 1 and including the retention cuff portion of FIGS. 1 and 2.

Turning now to the drawings, FIGS. 1-4 show one example of an inflationless retention cuff 50 constructed in accordance with the teachings of the present disclosure. In this example, the retention cuff 50 is best illustrated in FIGS. 2 and 3, while the cuff is shown attached to one example of a fecal collection device 52 depicted in FIG. 1. The configuration and construction of the fecal collection device 52 can vary within the scope of the present disclosure. In this example, the device 52 generally has a catheter or collection tube 54. One end 56 of the collection tube 54 has a tube shaped transphincter section 58 attached thereto, as shown in FIG. 3. The collection tube 54 can be formed of a relatively soft and flexible material and the transphincter section can be a relatively thin, soft, and flexible material so as to provide long term use capability. The softer materials of the tube 54 and transphincteric section 58 can reduce or minimize anal sphincter trauma to the patient for the hours or days that these products will be in use.

The inflationless retention cuff 50 can be coupled to the one end 56 of the collection tube 54, either directly to the one end or by connection to the transphincteric section 58, which is then connected to the one end as in this example. The other end 60 of the collection tube 54 in this example has a coupler 62 with a closure 64 attached. The coupler 62 can be configured to attach the device 52 to a collection bag (not shown) or other collection vessel to which the tube delivers collected fecal matter. The coupler can also be connectable to a suction device or the like for evacuating or emptying the collection tube 54, if and as needed. The closure 64 can be used to close and seal off the other end 60 when the collection tube 54 is not in use or not connected to a collection vessel. The fecal collection device 52 also has a lumen structure 66 that can include one or more lumens. For example, the lumen structure 66 can include an irrigation lumen 68 (see FIG. 3) used to deliver water or another irrigation liquid to the rectum of a patient and/or can include a lumen (not shown) to deliver medicine to the patient.

As noted above, the fecal collection device 52 can vary from the example shown and described herein. The basic structure of such a device is known and the disclosed inflationless retention cuffs can potentially be used with any such known collection device. The disclosed inflationless cuffs can also potentially be used on other types of medical fluid collection devices that are to be retained within an orifice of a patient. The disclosed inflationless retention cuffs need not be limited to only a fecal collection type device.

Figure 4:
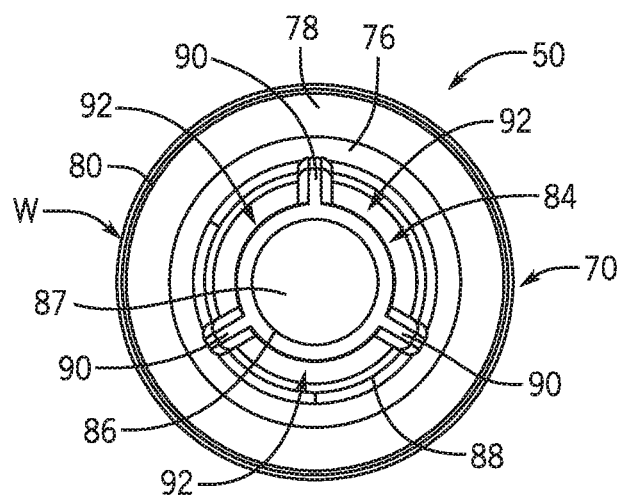
FIG. 4 shows an end view in the direction of the arrows 4-4 of the inflationless retention cuff portion of the device shown in FIG. 3.

As best illustrated in FIGS. 2-4, the inflationless retention cuff 50 in this example has a body 70 that can be one contiguous or integral piece formed of the same material. Alternatively, the body 70 can be formed of two or more separate pieces either formed of the same material or from different materials that are assembled to one another. The body 70 has a tube shaped neck portion 72 for connecting to the one end 56 of the collection tube 54 or to the transphincter section 58. The neck portion 72 defines at least part of a central opening 74 through the body. The central opening 74 forms or defines an axial flow path P along an axis of the body 70 aligned with the transphincter section 58. The body 70 also has abuse seal membrane or inflationless cuff wall W connected to the neck portion 72.

In this example, the membrane or wall W has an annular cuff wall 76 and a side wall 78. The annular cuff wall 76 extends radially outward from the neck portion 72 and thus radially outward relative to the transphincter section 58 and the one end 56 of the tube. In this example, the annular cuff wall 76 begins in a plane that is nearly perpendicular to or at a slight angle from perpendicular relative to the axial flow path P and central opening 74, as shown in FIG. 3. The thickness of the material that forms the inflationless cuff wall W varies, as discussed below. However, it is possible that the entire membrane or wall W or just the annular cuff wall 76 or the side wall 78 has a constant or substantially uniform material thickness. In the disclosed example, the thickness of the annular cuff wall 76 varies in a radial direction. The material thickness becomes gradually thinner moving away from the neck portion 72. Thus, the annular cuff wall 76 is sturdier nearer the neck portion 72 and becomes more flexible away from the neck portion.

The annular cuff wall 76 in this example gradually curves in an axial direction further away from the one end 56 of the collection tube 54 and transphincter section 58, as best shown in FIG. 3. In this example, the annular cuff wall 76 gradually transitions into the side wall 78, which is contiguous with the annular cuff wall. The side wall 78 in this example continues to curve such that a free or distal end 80 is oriented past parallel with the axial flow path P or axis of the body 70 until the side wall is slightly directed radially inward back toward the axial flow path. The side wall 78 of the body 70 terminates at the distal end 80, which creates an axial opening 82 into an end of the body 70 opposite the neck portion 72. The side wall 78 also varies in thickness in this example. The side wall 78 is thicker at the transition between the side wall and the annular cuff wall 76 and thinner at the distal end 80. The side wall 78 is thus more flexible at the distal end and relatively less flexible at the transition to the annular cuff wall.

In the disclosed example as shown in FIGS. 1-4, the annular cuff wall 76 and side wall 78 are one contiguous element and are defined as the aforementioned base membrane or inflationless cuff wall W. The combined cuff wall 76 and side wall 78, i.e., the inflationless cuff wall W, have a somewhat curved bowl or dish shape in this example. The inflationless cuff wall W, other than at and very near the distal end 80, thus has a smaller radius nearer the neck portion 72 and transphincter section 58 and an increasing radius moving radially away from the transphincter section. The inflationless cuff wall W is configured to funnel or direct fecal material toward the central opening 74 of the body 70 and into the transphincter section 58 in this example.

In this example, the body 70 of the retention cuff 50 also has a central core 84 or cage with a blunt nose 86 at a closed free end of the core as shown in FIGS. 3 and 4. The blunt nose 86 is a solid ball shaped element with a rounded leading end or tip 87. The tip 87 of the nose 86 defines the most distal part of the fecal collection device 52 and the retention cuff 50 in this example. The central core 84 also has and an open proximal end opposite the tip 87. The open proximal end forms a ring 88 that defines part of the central opening 74 of the body 70. The ring 88 is surrounded by the annular cuff wall 76 and side wall 78. The ring 88 of the central core 84 is integrally formed as part of the annular cuff wall 76 and is concentric with the axial flow path P in this example. If the retention cuff 50 were formed of more than one piece, the central core could be a separate piece connected to the cuff wall 76, the one end 56 of the tube, and/or the transphincter section 58. The ring 88 in this example has a frusto-conical shape that is narrower nearer the annular cuff wall 76 and wider spaced axially from the cuff wall. The ring 88 thus creates a tapered or funnel shape at an upstream end of the central opening 74 that can assist in funneling fluid from the body 70 along the central opening 74 to the neck portion 72.

The central core 84 also has a plurality of spars 90 or supports that extend axially along the core and connect the ring 88 to the nose 86. In this example, the central core 84 has three such spars 90, but the number can vary. A space 92 is defined between each pair of adjacent spars 90 and thus the central core 84 has three such spaces. The spaces 90 create axial flow openings or pathways on the body 70. These axial flow paths are generally perpendicular to the axial flow path P. The central core 84 is smaller in diameter than the diameter of the side wall 78 in this example. The blunt nose 86 of the central core 84 is substantially smaller in diameter. The spars 90 are not parallel with the axial flow path P but instead are angled in the axial direction. The spars 90 are closer to one another in a radial direction at the blunt nose 86 and are further apart in a radial direction at the ring 88. The spars 90 also have a size and shape in cross-section. The size and shape can be consistent over a length of the spar 90 or can vary. In the disclosed example, the spars 90 are thicker nearer the ring 88 and thinner nearer the blunt nose 86. Thus, the central core is narrowest at the tip 87 and wider nearer the ring 88.

During use, fluid or fecal matter can flow laterally into the retention cuff 50 through the spaces 92 between the spars 90 and then axially along the axial flow path P via the central opening 74. Fecal matter can also flow axially into the retention cuff 50 via the axial opening 82 within the perimeter of the side wall 78 and then through the spaces 92 to the central opening 74. The annular cuff wall 76 will seat against the rectal floor of a patient to create a seal when the collection device 52 is installed, as discussed in more detail below. Both the spaces 92 between the spars 90 and the axial opening 82 can pass fecal matter, fluid, or waste into the body 70 of the retention cuff 50. The inflationless cuff wall W, i.e., the side wall 78 and cuff wall 76 will collect and direct the fecal matter, fluid, and waste to the central opening 74 of the body and along the axial flow path P and into the collection tube 54.

The central core 84 and the annular cuff wall 76 and side wall 78 can be made of soft flexible material such as silicone or silicone rubber. The thickness of the blunt nose 86 and spars 90 can be much thicker than that of the inflationless cuff wall. The central core 84 thus can be relatively less flexible and forgiving in shape compared to the side wall 78 and cuff wall 76, though the spars 90 can have some flexibility, at least in a radial inward direction. The shape of the central core 84 in this example is tapered and somewhat similar to a suppository. Thus, the inflationless cuff wall W can be deformed, as can the spars 90, for easy insertion into the patient without the central core becoming significantly deformed. Each will then spring back or self-deploy back to the normal shape upon insertion in the patient. The relatively stiff but resilient central core 84 and the flexible but resilient inflationless cuff wall W will help the retention cuff 50 retain its shape during use. The spars 90 can have a relatively thick profile to aid in maintaining the central core 84 shape, as shown in FIG. 3. The proximal end or ring 88 of the central core 84 can also be thicker than the adjacent annular cuff wall 76 to help prevent the central opening 74 from collapsing as a patient moves about. In patient, the multiple spaces 92 of the central core 84 will aid in preventing the retention cuff 50 from becoming completely occluded during use and will help keep the collection tube aligned within the patient's anus and open to flow. The annular cuff wall 76 and side wall 78 can again easily be collapsed to a reduced diameter for relatively easy removal from the patient.

As noted above, the central core 84 or cage and the inflationless cuff wall W can be formed as a unitary integral structure from the same material or can be formed as two pieces. The central core 84 can be formed of a relatively rigid or stiff material or, as described herein, can have greater wall thickness but be formed of a soft flexible material such as silicone. The thicker portions, such as the closed end or blunt nose 86 and the spars 90 can still render the structure sufficiently rigid. The base seal membrane or inflationless cuff wall W should be flexible and resilient.

FIGS. 5-7 depict another example of a retention cuff 100 constructed in accordance with the teachings of the present disclosure. In FIG. 5, the retention cuff 100 is again depicted as being connected to the transphincter section 58 of a fecal collection device 52. In this example as shown in FIGS. 6 and 7, the retention cuff 100 has a body 102 with a neck portion 104 that is joined to the free end of the transphincter section 58. The body 70 also has an inflationless cuff wall W that is somewhat similar to the earlier described wall for the prior example shown in FIGS. 1-4. The inflationless cuff wall W has an annular wall 106 that extends radially outward from the neck portion 104 and thus the transphincter section 58 and the one end 56 of the collection tube 54. The cuff wall W also has a side wall 108 that transitions from the annular cuff wall 106 in an axial direction. The body 102 again has a central opening 110 that forms the axial flow path P and that is defined at least in part by an axis of the neck portion 104. The inflationless cuff wall W again provides the seal within the patient's body to prevent leakage of fluids and fecal matter.

In this example, the annular cuff wall 106 begins in a plane that is perpendicular or nearly perpendicular to the neck portion 104 and the axial flow path P. The annular cuff wall 106 gradually curves axially away from the transphincter section 58 and the one end 56 of the collection tube 54 and transitions into the side wall 108. In this example, the annular cuff wall 106 has a generally constant material thickness. The side wall 108 extends in an axial direction away from the transphincter section 58 and the one end 56 and continues to curve until it is again directed radially inward back toward the axial flow path P. The side wall 108 of the body 102 terminates at a free or distal end 112 of the inflationless cuff wall W and forms an axial opening 114 into the body. The inward curve at the distal end 112 forms a radial in turned lip 116 at the axial opening 112 into the retention cuff 100 in this example. The thickness of the side wall 108 in this example is relatively consistent over the lower portion of the side wall at the transition to the annular cuff wall 106 and is about the same as the thickness of the cuff wall. The thickness of the side wall 108 becomes thinner approaching the distal end 112.

The body 102 of the retention cuff 100 depicted in FIGS. 5-7 can be fabricated from any suitable material that is flexible and resilient, such as silicone or silicone rubber. The inflationless cuff wall W, i.e., the annular cuff wall 106 and the side wall 108 can be deformed from the undeformed shape depicted in FIGS. 5-7 to insert the retention cuff into a patient. A user can place their finger inside the body 102 to push the deformed retention cuff 100 into the patient's rectum. The retention cuff 100 will spring back or self-deploy to its normal, non-deformed shape when inserted into the patient. The retention cuff 100 can also deform as needed during use within the patient. However, with the shape of the side wall 108 and annular cuff wall 106 and the size of the axial opening 114 into the body 102, the retention cuff 100 and axial opening will not be susceptible to becoming completely occluded. The inflationless cuff wall W can seat against the rectal floor to create a seal when installed. The axial opening 114 will direct fluid, waste, or fecal matter into the body 102, which will then direct the fluid, waste, or fecal matter into the central opening 110 and along axial flow path P to the collection tube 54.

The wall thickness of the inflationless cuff wall W can be thicker near the annular cuff wall 106 and the thickness can vary, as in the previously described example of FIGS. 1-4. Also, the selected material for the inflationless cuff wall W and the neck portion 104 can have a sufficiently high durometer so that the retention cuff 100 resists collapse after insertion in a patient and during use. The outside diameter of the retention cuff 100 of FIGS. 5-7 can also be smaller in diameter than a traditional inflatable cuff. This can further reduce collapse of the cuff during use. To insert the retention cuff 100, the lip 116 surrounding and defining the axial opening 114 into the cuff body 102 can act as a natural finger pocket to aid with insertion, as noted above. The inflationless cuff wall W of the retention cuff 50 can also be constructed similar to that of the retention cuff 100, if desired.

In the example of FIGS. 5-7, the retention cuff does not have a central core like the core 84 of the earlier described retention cuff 50. Also, if a retention cuff has a central core, the core can vary in configuration and construction from that of the central core 84 described earlier. FIGS. 8-16 depict several alternative designs for a central core or cage for an inflationless retention cuff. In each of these alternative examples, the central core is shorter than the central core 84 for the retention cuff 50 shown in FIGS. 1-4. The central core 84 on the retention cuff 50 extended well beyond the distal end 80 of the inflationless cuff wall W. In these examples, the alternative cores extend only to about the level of approximately the distal end of the inflationless cuff wall W (see FIGS. 10, 13, 16).

Figure 8:
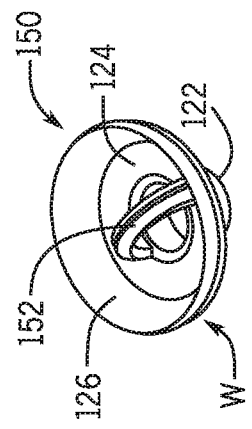
FIGS. 8-10 show perspective, top, and side views of another example of an inflationless cuff portion for a device such as that of FIG. 1 and constructed in accordance with the teachings of the present invention.
Figure 11:
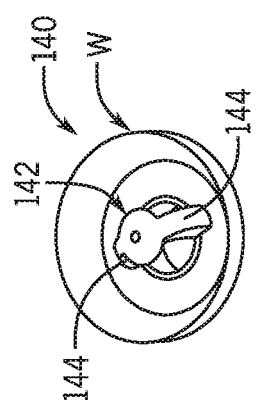
FIGS. 11-13 show perspective, top, and side views of another example of an inflationless cuff portion similar to that of FIGS. 8-10 for a device such as that of FIG. 1 and constructed in accordance with the teachings of the present invention.
Figure 14:
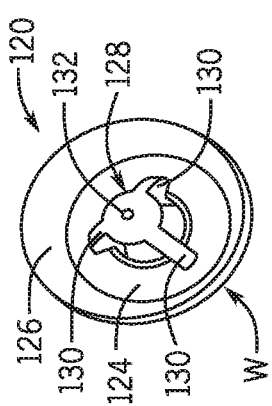
FIGS. 14-16 show perspective, top, and side views of another example of an inflationless cuff portion similar to that of FIGS. 11-13 for a device such as that of FIG. 1 and constructed in accordance with the teachings of the present invention.
Figure 9:
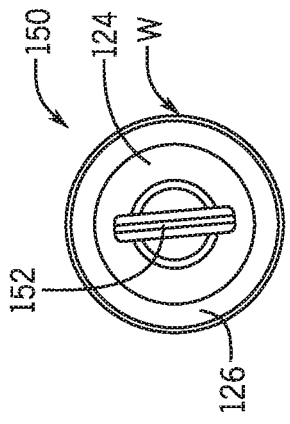
Figure 12:
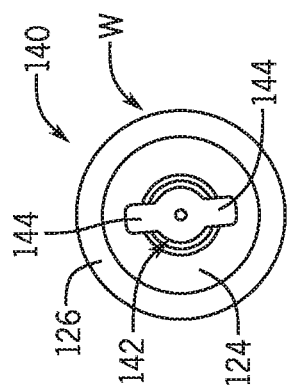
Figure 15:
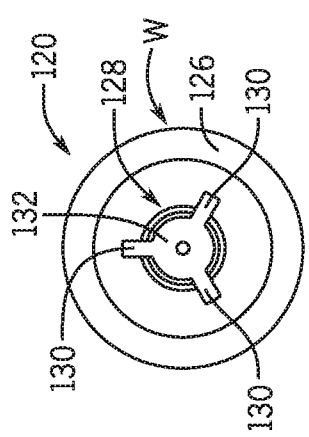
Figure 10:
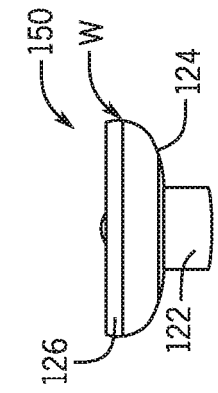
Figure 13:
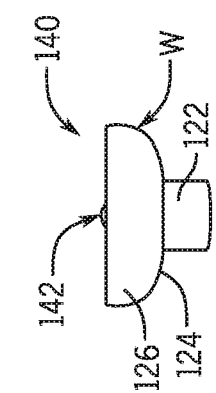
Figure 16:
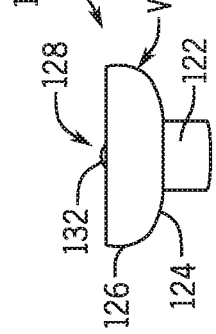

FIGS. 8-10 show a retention cuff 120 with a body having a neck portion 122 and an inflationless cuff wall W. The cuff wall W has an annular cuff wall 124 and a side wall 126, which can be similar to those described above. The retention cuff 120 also has a central core 128 of this shorter height type. The central core 128 has three spars 130 connecting a rounded blunt nose 132 to the annular cuff wall 126. FIGS. 11-13 show another alternative example of a retention cuff 140 with a central core 142 with only two such spars 144. The retention cuff 140 with only the two spars 144 may provide an advantage of larger lateral flow paths to the central opening of the retention cuff FIGS. 14-16 show yet another alternative example of a retention cuff 150 with a central core 152 that is formed as a curved bridge or simple arch over and across the central opening. The central core 152 has no blunt nose. The bridge or arch shape of the central core 152 again creates two lateral flow paths into the central opening of the retention cuff 150. A further potential advantage of each of these shorter central core alternatives is in substantially free access to the collection tube entrance at the level of the annular cuff wall 124 in each example. This is because there is no raised ring, such as the ring 88 on the earlier described central core 84. A still further potential advantage is simply a less massive foreign body present in the rectum of a patient. In each of these example, the central cores, though smaller, can still aid in preventing complete occlusion of the central opening of the cuff during use.

Figure 18:
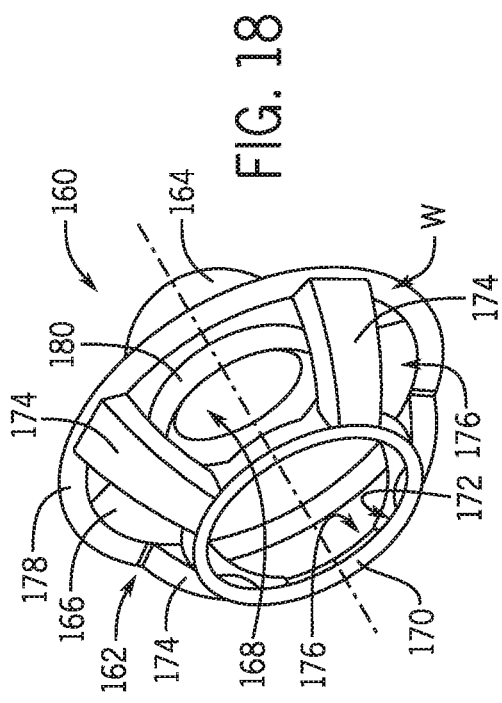
FIG. 18 shows an enlarged perspective view of an inflationless retention cuff portion of the device shown in FIG. 17 and constructed in accordance with the teachings of the present invention.
Figure 20:
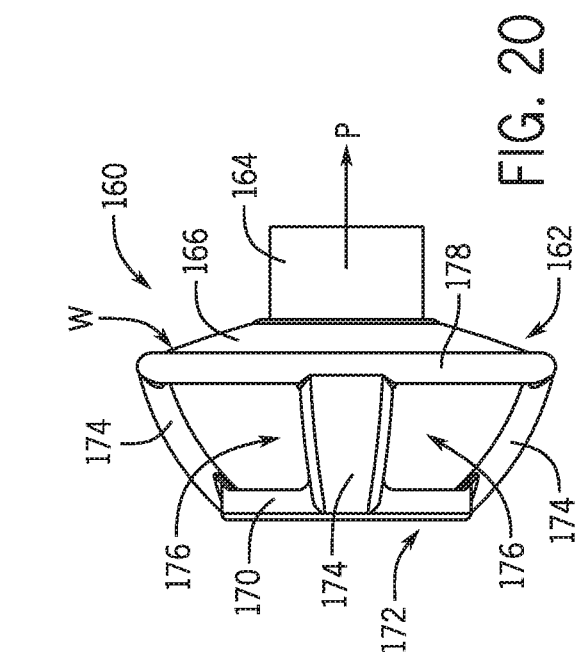
FIG. 20 shows a side view of the retention cuff portion shown in FIG. 18.
Figure 17:
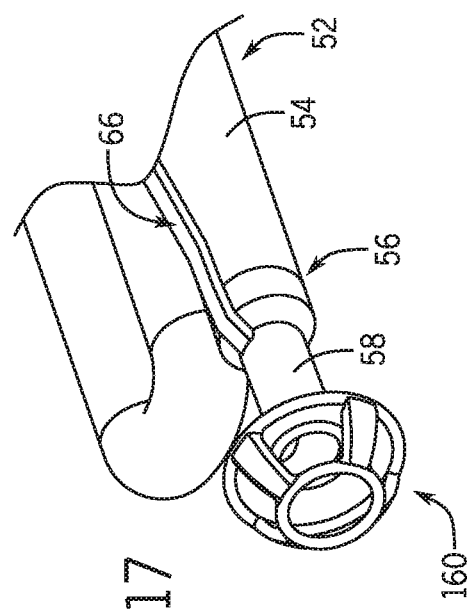
FIG. 17 shows a perspective view of a portion of another example of a fecal collection device constructed in accordance with the teachings of the present invention.
Figure 19:
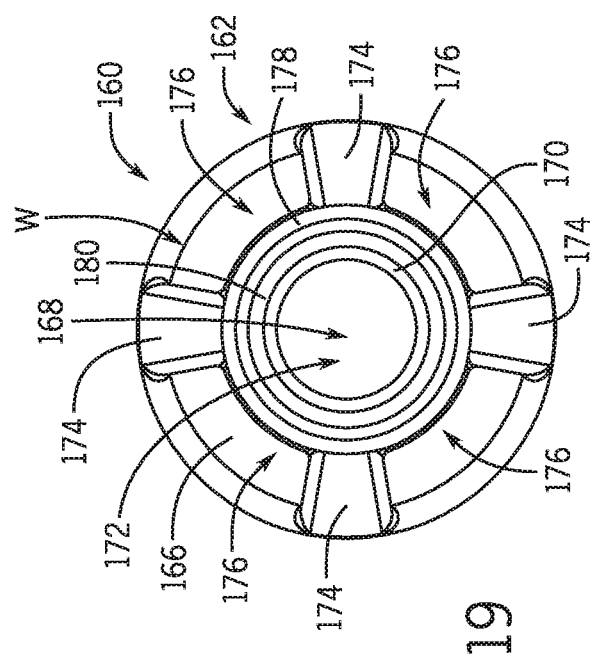
FIG. 19 shows an end view of the retention cuff portion of FIG. 18.

FIGS. 17-20 depict another example of an inflationless retention cuff 160 constructed in accordance with the teachings of the present invention. In this example, the retention cuff 160 is again depicted in FIG. 17 as part of a fecal collection device 52. In this example as depicted in FIGS. 18-20, the retention cuff 160 has a body 162 that is of a one piece contiguous construction. The body 162 includes a neck portion 164 for connecting to the one end 56 of the collection tube 54 or the transphincter section 58 on the device 52. The body 162 also has a retention cuff membrane or inflationless cuff wall W with an annular cuff wall 166 that extends radially outward from the neck portion 164 and thus the transphincter section 58 and the axial flow path P. In this example, the annular wall 166 resembles a Belleville washer and has a frusto-conical shape. The wall surface is not curved in the radial direction, unlike the earlier described examples. The annular wall 166 surface does, however, lie at an angle from perpendicular relative to the axial flow path P of the collection tube 54 and a central opening 168 defined by the neck portion 164. The material thickness across the annular cuff wall 166 can be consistent or can vary in a radial direction. The annular cuff wall 166 in this example is again configured and arranged to funnel fecal material, fluid, or waste toward the central opening 168 of the neck portion 164 as welt as to create a seal against a patient's rectal wall to prevent leakage when installed.

The inflationless cuff wall W in this example also has an upper ring 170 spaced axially from the annular cuff wall 166. The upper ring 170 is open at the center and defines an axial opening 172 at the end of the body 162 into the retention cuff 160. Fluid, waste, or fecal matter can flow axially into the body 162 of the retention cuff via the axial opening 172. The inflationless cuff wall W also has a plurality of spars 174 or supports that connect the upper ring 170 to the annular cuff wall 166. There are four such spars 174 in this example, though again there could be more or fewer spars. The plurality of spars 174 extend in an axial direction but are again not parallel to the axial flow path P of the retention cuff 160. Instead, the spars 174 are radially closer to one another at the upper ring 170 and radially further apart at the annular cuff wall 166.

A plurality of spaces 176 are formed between adjacent spars 174 and create lateral or radial flow openings or pathways that are perpendicular to the axial flow path P of the retention cuff 160. Fecal matter can flow laterally into the retention cuff 160 through the spaces 176 between the spars and then axially along the axial flow path P into the central opening 168 to the collection tube 54. As noted above, fecal matter can also flow axially through the axial opening 172 into the body 162. The annular cuff wall 166 can seat against the rectal floor of a patient to create a seal when installed. The axial opening 172, spaces, 176, and annular cuff wall 166 will collect and direct fecal matter, fluid, and waste into the central opening 168 and along the axial flow path P to the collection tube 54 of the device 52. The inflationless cuff wall W of the retention cuff 160 in this example forms a cage-like structure, somewhat similar to the earlier described central core examples. The entire body 162 can be formed of a single flexible and resilient material such as silicone or silicone rubber. The upper ring 170 and spars 174 can assist in the cuff 160 holding its shape during use and yet can allow the cuff to be deformed for easy insertion and removal.

In this example, the annular cuff wall 166 can also have a thicker bead or integral lower outer ring 178 around its perimeter. Such a ring 178 can assist in the annular cuff wall self-deploying after being deformed and inserted into a patient. The spars can be connected to the outer lower ring 178 as in this example. An integral lower inner ring 180 can be provided on the annular cuff wall 166 and surrounding the central opening 168 into the neck 164 of the body 162. The lower rings 178, 180 can be employed to add some structural rigidity and resiliency to the otherwise flexible and thin annular cuff wall 166 and to aid in preventing complete occlusion of the central opening 168 during use. The diameter of the lower outer ring 178 and the perimeter of the annular cuff wall 166 are larger than the diameter of the upper ring 170. This gives the retention cuff a frusto-conical shape.

In this example, the spars 174 are wider in a circumferential direction and thinner in a radial direction when compared to earlier described spars. This serves to illustrate that the configuration and construction of the various retention cuffs and the optional spars can vary. FIGS. 21-23 show another similar example of an inflationless retention cuff 190. In this example, the retention cuff has essentially the same overall structure as the cuff 160 in FIGS. 17-20. However, the supports or spars 192 have an even thinner wall thickness and a wider profile in the circumferential direction. The spars 192 are also curved slightly inward or concavely toward the axial flow path P, whereas the spars 174 of the cuff 160 are curved slightly convexly in the axial direction. Again, this serves to illustrate that the configuration of the inflationless cuffs disclosed and described herein can vary in shape and contour while falling within the scope of the disclosure. This is applicable to any of the disclosed examples.

FIGS. 24-26 show yet another example of an inflationless retention cuff 200 that is very similar to the cuff 160. However, in this example, the upper ring 202 is a separate part that attaches to free ends 204 of the spars 206 or supports after each is manufactured. The upper ring 202 can be attached to the spars 206 by molecular bonding, chemical bonding, adhesive bonding, welding, or the like. As shown, the spars 206 can have tongues or tabs 208 extending from the free ends 204. These can seat in a groove (not shown) formed in the upper ring. Adhesive, for example, can be applied to portions of the tabs or the groove to avoid exposing adhesive in the assembled cuff. In another example, the upper ring and spars can be separately manufactured as one piece and the annular cuff wall 210 can be fabricated as another part to be attached to one another. Alternatively, the cuff 200 could be formed as two separate parts that attach axially with the separation between or lengthwise along two of the spars, i.e., a sagittal section. By separating the cuff 200 into two or more separate pieces, manufacture of the cuff parts can be made easier by allowing the cuff to be released from a mold tool without having to stretch any portion of the cuff, and particularly the upper ring, to clear larger portions of the mold.

In this example, a flange 212 is also provided that depends downward from the upper ring 202. The flange 212 can be used to help with insertion of the retention cuff into a patient, in the manner discussed below. The flange 212 may be provided to help catch the fingertip of a technician and prevent the tip from slipping out of the cuff or off of the upper ring during insertion of the cuff into a patient.

Figure 29:
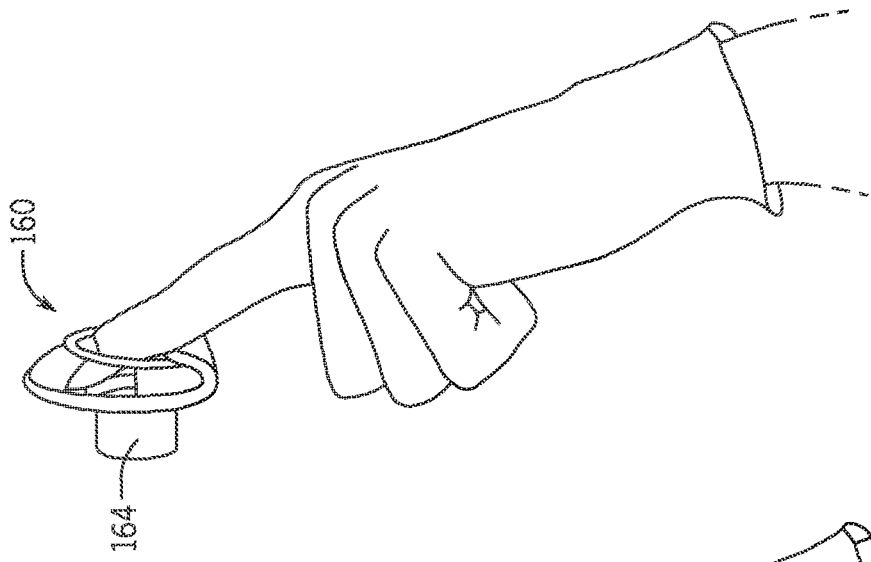
FIGS. 27-29 show an example of one method of inserting an inflationless retention cuff portion such as the examples depicted in FIGS. 17-20 or FIGS. 24-26.
Figure 28:
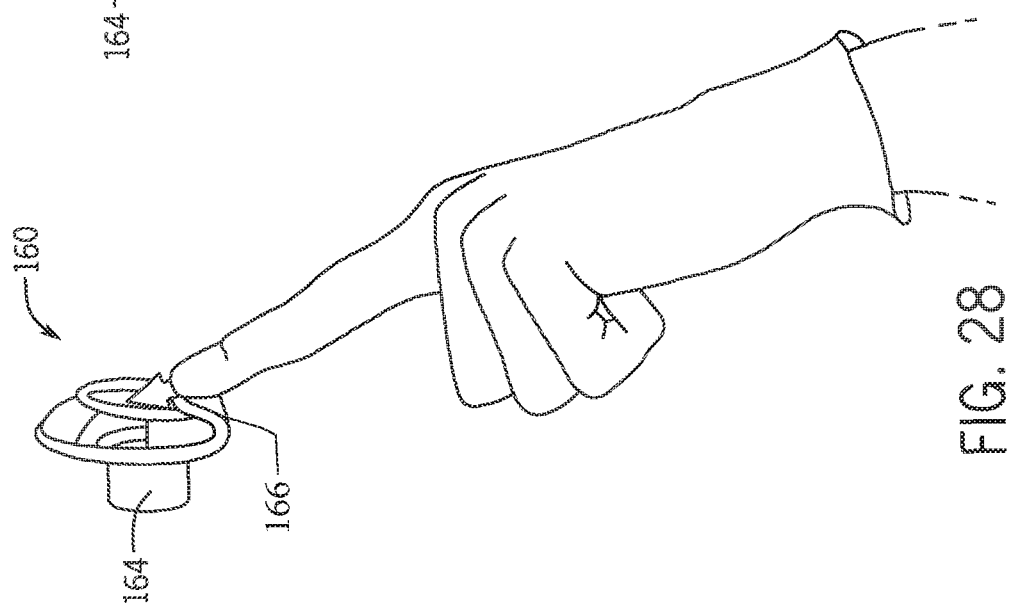
Figure 27:
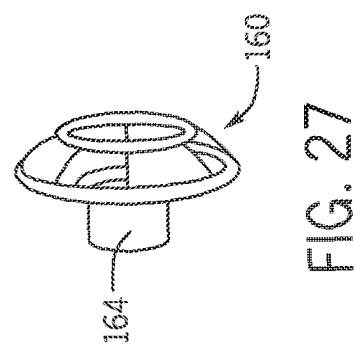

FIGS. 27-29 show one example of an insertion method for inserting the disclosed retention cuffs. In this example, the retention cuff 160 of FIGS. 17-20 is shown in its deployed state in FIG. 27. A technician can use their finger to fold up part of the cuff 160, such as the annular cuff wall 166 as shown in FIG. 28. The technician can then further insert their finger into or across the axial opening 172 of the upper ring 170 to hook onto the cuff as shown in FIG. 29. In this example, the finger is seated at the juncture between one of the spars 174 or supports and the annular cuff wall 166 opposite the folded side of the cuff wall. The technician can then push the retention cuff 160 and the adjacent, connected portion of the collection tube 54 and transphincter section 58 into the anus of the patient.

The retention cuffs disclosed herein can be folded in other ways, different from the example shown in FIGS. 27-29. The technician's finger can also hook onto a different portion of the cuffs as well, depending on the particular configuration of the retention cuff. In the example of FIGS. 5-7, the finger can hook under the lip 116 of the side wall 108. In the example of FIGS. 1-4, the technician's finger can push against an underside of the blunt nose 86 on the central core 84 for insertion. In the example of FIGS. 24-26, the technician's finger can hook under the flange 212 on the upper ring 202.

In each of the inflationless cuff examples disclosed herein, the annular cuff wall can be designed in conjunction with the rest of the cuff body, such as the neck portion and/or the side wall, to aid in keeping a seal within the anal canal of a patient to prevent leakage. The free or distal end of the cuff body and the side walls or spars/supports can be configured, through resiliency of the material and size and shape of the body, to bias the annular cuff wall against the rectal floor. When the inflationless retention cuff is in place within the patient, the distal end of the body can engage a wall of the rectum under slight compression. This will urge the side wall, upper ring, spars/supports, and/or other central core or inflationless cuff wall to extend toward the rectal floor. This force will in turn bias the annular cuff wall against the rectal floor to help prevent leakage around the outside of the retention cuff and collection tube and/or transphincter section.

Figure 30:
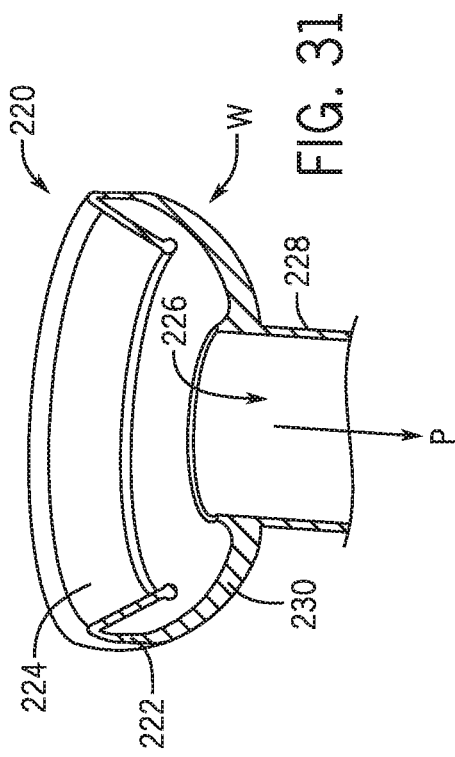
FIG. 30 shows an enlarged perspective view of another example of an inflationless retention cuff portion of a device such as that shown in FIG. 1 and constructed in accordance with the teachings of the present invention.
Figure 31:
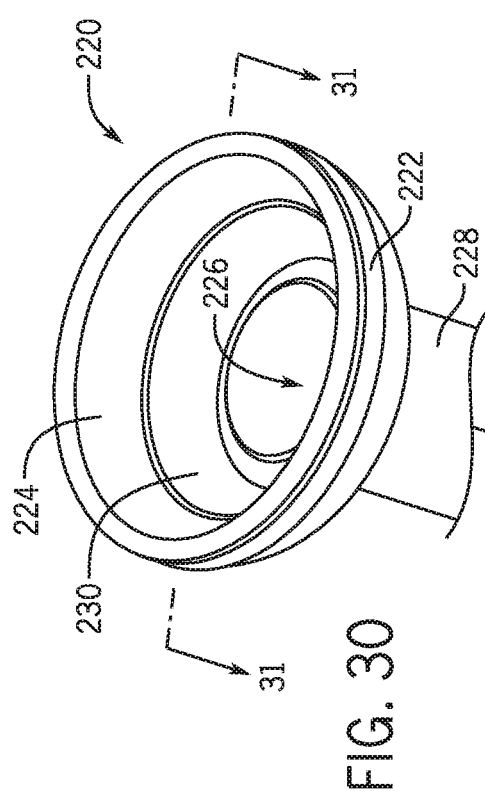
FIG. 31 shows a cross-section taken along line 31-31 of the retention cuff portion shown in FIG. 30.

FIGS. 30 and 31 depict another example of an inflationless retention cuff 220 constructed in accordance with the teachings of the present invention. This retention cuff 220 is similar to the retention cuff 100 shown in FIGS. 5-7. However, the side wall 222 in this example does not terminate at the axial opening 114 and does not have the lip 116 of the cuff. Instead, a return flange 224 is formed extending from the distal end 226 of the side wall 222 and extends radially inward and spaced from the side wall back toward a central opening 226 and a neck portion 228 of the cuff 220. This return flange also extends in an axial direction back toward the annular cuff wall 230 on the inflationless cuff wall W. The return flange 224 can provide a finger pocket for a technician's finger when the cuff 220 is folded and then inserted into a patient. The return flange 224 can also add some structural integrity to the otherwise flexible cuff body.

Figure 32:
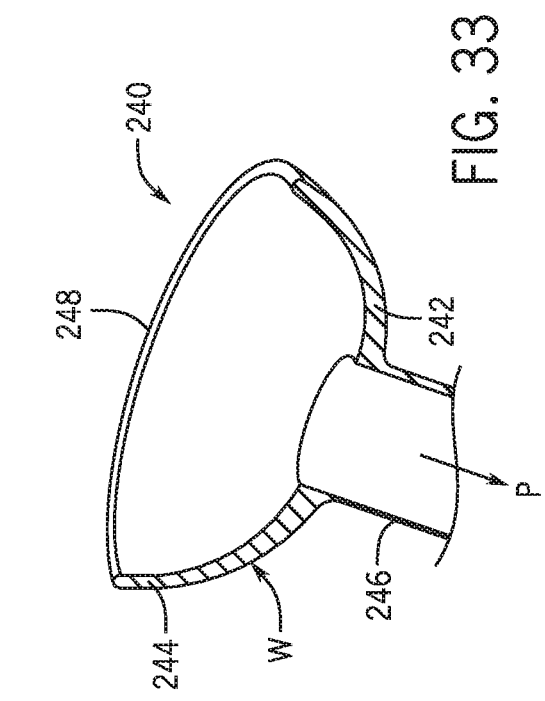
FIG. 32 shows an enlarged perspective view of another example of an inflationless retention cuff portion of a device such as that shown in FIG. 1 and constructed in accordance with the teachings of the present invention.
Figure 33:
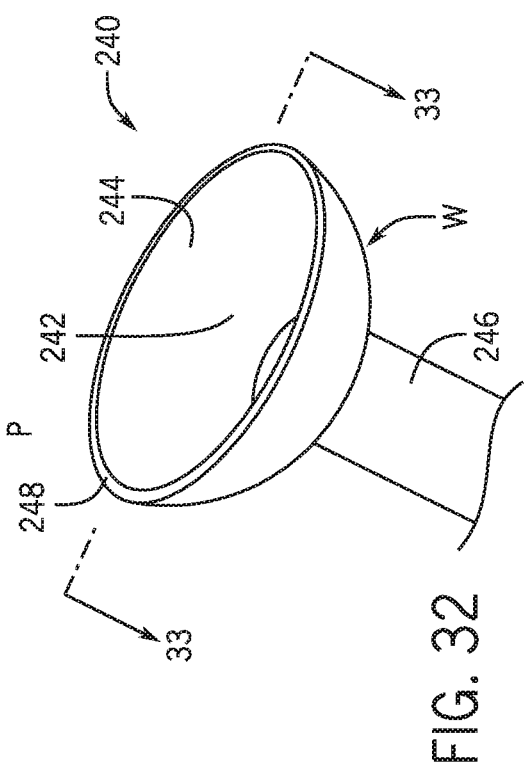
FIG. 33 shows a cross-section taken along line 33-33 of the retention cuff portion shown in FIG. 32.

FIGS. 32 and 33 depict yet another example of an inflationless retention cuff 240 constructed in accordance with the teachings of the present invention. This cuff 240 is in similar to the retention cuff 100 of FIGS. 5-7. However, in this example, the inflationless cuff wall W has a slightly different shape or contour. In this example, an annular cuff wall 242 and side wall 244 are contiguous and have a relatively consistent curvature from a neck portion 246 of the cuff 240 to a distal end 248 of the side wall. The inflationless cuff wall W essentially has the shape of a portion of a sphere in this example. The examples in FIGS. 30-33 are shown herein to illustrate that the specific configuration and construction of the annular cuff wall and the side wall portion, if present, of the disclosed retention cuffs can vary.

FIGS. 34 and 35 depict another example of an inflationless retention cuff 250 constructed in accordance with the teachings of the present invention. In this example, a body 252 of the cuff 250 is more similar to a conventional inflatable spheroid-like retention cuff as is known in the art. In this example, the inflationless cuff wall W has an annular cuff wall 254 extending from a neck portion 256 and has a side wall 258 that transitions from the cuff wall, as in the prior examples. In this example, the side wall 258 has a distal end that further transitions into amore distinct top wall 260. The side wall 258 has a larger axial dimension in this example. The top wall 260 has a smaller axial opening 262 providing a flow path into the cuff body 252 in comparison to a number of the earlier examples. In this example, the side wall 258 also has a plurality of through holes 264 that create lateral flow pathways into the cuff body 252. Thus, in this example, fluid, waste, or fecal matter can flow in an axial direction through the axial opening 262 into the cuff body 252 and in a radial or lateral direction through the one or more holes 264 into the cuff body. If the retention cuff is partially occluded axially, radially, or both, flow can still take place through any one or more of the non-occluded openings in the body 252.

FIG. 36 shows another retention cuff 270 that is essentially the same as the retention cuff 250, but without the optional through holes 264 in the side wall 272 of the cuff. FIG. 37 shows another very similar retention cuff 280. However, in this example, the cuff 280 has elongate vertical slots 282 formed through the body material and partly along the side wall 284 and partly along the top wall 286. The slots 284 can again form secondary axial and lateral or radial flow paths into the cuff body.

FIGS. 38 and 39 show still additional examples of other inflationless retention cuff shapes that are within the scope of the present invention. FIG. 38 shows a retention cuff 290 with an inflationless cuff wall W that is quite similar to that of the retention cuff 50 in FIGS. 1-4. However, in this example, the retention cuff 290 has no central core. The inflationless cuff wall W of the retention cuff 290 has an annular cuff wall 292 and a side wall 294. FIG. 39 shows a retention cuff 300 that is quite similar to the retention cuff 270 shown in FIG. 36. The retention cuff 300 has an inflationless cuff wall W with an annular cuff wall 302 and a side wall 304. In each example, the annular cuff wall 292 and 302 is oriented at more of an angle in the axial direction than in the comparatively similar examples. FIG. 40 shows still another example of an inflationless retention cuff 310 that is quite similar to the retention cuff 290 of FIG. 38. However, the retention cuff 310 has one or more notches 312 formed in a distal end 314 of the side wall 316 adjacent an axial opening 318 defined by the distal end into the cuff body. The notches 312 can create secondary flow channels or pathways laterally or radially into the cuff body for when the retention cuff 310 is otherwise occluded or partially occluded.

Figure 41:
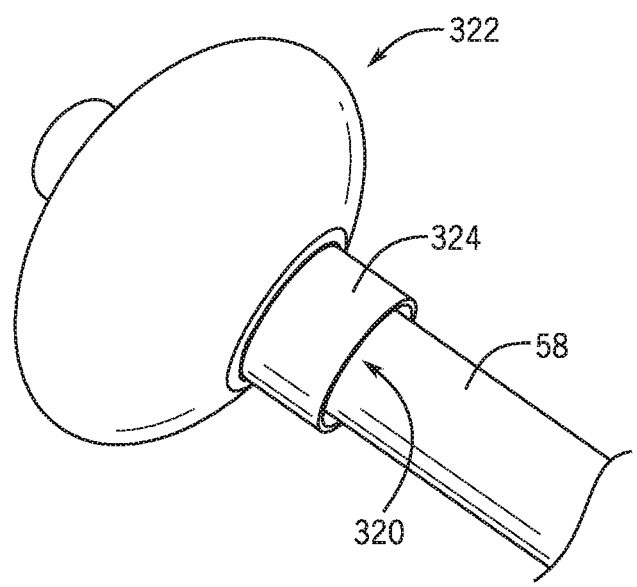
FIG. 41 shows a perspective view of a portion of a fecal collection device with one example of an insertion aid for the device.

In each of the disclosed retention cuff examples, the fecal collection device 52 can be provided with a separate insertion aid adjacent the retention cuff. FIG. 41 shows one example of such an insertion aid. In this example, the fecal collection device 52 is provided with a finger pocket 320, i.e., a gap at the joint between a retention cuff 322 and the transphincter section 58 or the one end of the collection tube. The insertion aid in this example is a finger pocket 320 into which a medical technician can insert their finger in order to push the retention cuff into the anus of a patient. The finger pocket in this example is in the form of a 360° skirt 324 at the base of the inflationless retention cuff 322. The skirt 324 creates a hooded space between the skirt and the neck portion of the cuff or the transphincter section 58 or the one end of the collection tube. The finger pocket 320 can be accessed by deforming the adjacent collection tube, transphincter section, or cuff neck portion. The finger pocket 320 can make it easier for the technician to insert the fecal collection device 52 and to push the retention cuff 322 into the anus of a patient. The insertion aid or finger pocket 320 of FIG. 41 can be used on virtually any of the inflationless retention cuffs and fecal collection devices disclosed herein.

Each retention cuff example disclosed herein has an inflationless cuff wall with at least an annular cuff wall portion and aside element such as the spars or the side walls. The annular cuff wall can seat against the rectal floor of a patient to create a seal to prevent leakage of fecal matter from the patient. The flexibility and resiliency of the disclosed retention cuffs can adjust, change, and adapt upon contact with surfaces within a patient's rectal vault as those surfaces move and change with patient movement. Further, even if part of the cuff were to succumb to pressure and occlude, the disclosed retention cuffs are configured to resist complete occlusion. Some of the cuffs have a relatively large axial opening, making it difficult to become completely blocked or occluded. Other of the cuffs have one or more, lateral openings, slots, sub-channels, pathways, notches, or the like in the side elements that will remain open and flowing. With current, known designs, it may be that, during use, the opening into the rectal space of the patient is or becomes generally perpendicular to the opening into the transphincter section. In such a condition, the rectal wall can occlude the opening into the transphincter section. With the disclosed retention cuff designs, either one or more of the secondary lateral openings or flow pathways in the cuff, or at least part of the larger axial opening into the cuff, will still open into the transphincter section and will generally align with the opening into the rectal space, thereby providing an unobstructed effluent flow path. The annular cuff wall and neck portion will also aid in retaining the transphincter section at least party open to flow as well. Thus, the disclosed inflationless retention cuffs can aid in preventing complete occlusion of the catheter during use as a patient moves and shifts position.

The effluent conduit or collection tube at the one end can be sealed to a thinner, soft, and flexible transphincter section, as in a number of the above-described embodiments. The disclosed retention cuffs can then be attached to the transphincter section. However, the disclosed retention cuffs can also be connected directly to the effluent or collection tube, if desired. It is possible that the disclosed inflatable retention cuffs can be attached via a stiffer annulus to the collection tube, if desired. However, the disclosed cuff designs can eliminate the need for an annulus.

As shown in FIGS. 1-41, the disclosed inflationless retention cuff configurations are quite different from prior known designs, which are typically somewhat spherical or round, are inflatable, and have a continuous rounded end face leading into the rectal catheter lumen or annulus. The disclosed retention cuffs can be larger in size than a conventional retention cuff. This is because the larger size will not likely irritate the patient because the retention cuffs are not inflated to a turgid condition. The disclosed retention cuffs can also eliminate the need for the stiffer annulus because the retention cuff designs can help retain the open flow shape of the transphincter section or collection tube attached to the cuff. However, the disclosed inflationless cuffs will likely perform better at the same general size or diameter as a conventional inflatable cuff. Further, inflationless designs such as those disclosed herein may be substantially smaller than currently available inflated cuffs and still function as intended or even offer improved performance. Most of the disclosed retention cuffs also have a non-spherical end face shape and are, at least in part, resilient and flexible. Thus, the cuffs can assume different shapes to fill and conform to a range of rectal ampulla sizes and shapes. The disclosed retention cuffs can also adapt to the changing shape of the anal canal as a patient moves.

The disclosed retention cuff shapes can also be distinctive in the marketplace and provide differentiation from competitive products simply by the irregular appearance of the retention cuff shape. The disclosed retention cuffs will also outperform competitive products because the cuffs will provide a much better seal within the anal canal and will better conform and adapt to patient movements, adapt to patient muscle contraction and relaxing, and accommodate a broader range of patient body sizes and shapes. This in turn can help maintain an internal seal and avoid the retention cuff causing anal vein abrasion and bleeding, First, the retention cuff being somewhat flexible instead of turgid allows the cuff to be deformed by the anatomical features of the rectal ampulla of the patient. Second, the retention cuff being uninflated will apply less internal pressure to rectal venules and capillaries.

The disclosed retention cuffs each is described as having a central opening. The term central is used herein to determine that the opening is positioned to be in flow communication with the collection tube of a fluid collection or fecal collection device. The opening need not be at a center of the retention cuff, such as if the retention cuff were to have an irregular or non-round or circular perimeter shape.

Bowel management systems and rectal catheters of the type described herein, for which the disclosed retention cuff may be useful, are disclosed in, for example, U.S. Pat. Nos. 8,323,255, 8,075,540, 7,722,583, and 7,147,627, which are incorporated herein in their entireties.

In the various embodiments, like reference numbers used in different examples are intended to signify either an identical or substantially similar part among the different examples. Also, various features, aspects, characteristics, and components are disclosed herein in different combinations among the various disclosed examples. These various features, aspects, characteristics, and components may be employed independent of one another or in other combinations though not specifically disclosed herein.

Although certain inflationless retention cuffs, fecal and fluid collection devices, cuff body configurations, and insertion and other methods of use have been described herein in accordance with the teachings of the present disclosure, the scope of coverage of this patent is not limited thereto. On the contrary, this patent covers all embodiments of the teachings of the disclosure that fairly fall within the scope of permissible equivalents.

What is claimed is:

1. A fecal collection device comprising:
a retention cuff having a non-inflatable body including a neck portion,
a central opening through the neck portion, and
an inflationless cuff wall having at least an annular cuff wall extending radially outward from the neck portion and having a side wall that is angled in an axial direction away from the central opening and curves until it is directed radially inward back toward the central opening, the side wall having a distal end that defines a perimeter outer edge of the inflationless cuff wall, the annular cuff wall and the side wall of the inflationless cuff wall gradually and continuously decreasing in thickness from the neck portion to the distal end of the side wall, the inflationless cuff wall surrounding the central opening and having an undeformed shape configured to direct collected fecal matter to the central opening.

2. A fecal collection device according to claim 1, wherein the annular cuff wall has a generally frusto-conical shape or a funnel shape and defines at least part of the portion that is angled in the axial direction.

3. A fecal collection device according to claim 1, wherein the inflationless cuff wall has a generally curved bowl shape or curved dish shape.

4. A fecal collection device according to claim 1, wherein at least part of the side wall extends axially away from the central opening and defines an axial opening into the body, the side wall having one or more radial flow path-ways formed laterally into the body.

5. A fecal collection device according to claim 4, wherein the one or more radial flow pathways are defined by one or more openings, sub-channels, or slots formed through the side wall.

6. A fecal collection device according to claim 1, further comprising a plurality of spars extending in an axial direction away from the central opening, the plurality of spars forming one or more lateral flow pathways therebetween into the cuff body.

7. A fecal collection device according to claim 6, wherein the plurality of spars is joined to the annular cuff wall radially inward of the perimeter outer edge of the inflationless cuff wall.

8. A fecal collection device according to claim 1, wherein the retention cuff has a central core with a plurality of spars forming one or more lateral flow pathways into the cuff body.

9. A fecal collection device according to claim 8, wherein the central core is a part of the body.

10. A fecal collection device according to claim 8, wherein the central core is positioned axially aligned with the central opening and is a part of the body positioned radially inward of a perimeter edge of the annular cuff wall.

11. A fecal collection device according to claim 1, wherein at least the inflationless cuff wall is formed of a resilient flexible material that can be physically deformed from the undeformed shape by an applied force upon the inflationless cuff wall and that will return to the undeformed shape when not subjected to the applied force.

12. A retention cuff for retaining a fluid collection device or system in an orifice of a patient, the retention cuff having a central opening and a body with an inflationless cuff wall that includes an annular cuff wall and a side wall that is angled in an axial direction away from the central opening and curves until it is directed radially inward back toward the central opening, the side wall having a distal end that defines a perimeter outer edge of the inflationless cuff wall, the annular cuff wall and the side wall of the inflationless cuff wall gradually and continuously decreasing in thickness from the central opening to the distal end of the side wall, the inflationless cuff including one or more side elements, the retention cuff being non-inflatable and having a self-deployed state or shape.

13. A retention cuff according to claim 12, wherein the one or more side elements includes a plurality of spars connected to and extending in an axial direction from the annular cuff wall.

14. A retention cuff according to claim 12, further comprising one or more lateral flow path openings through or between the one or more side elements.

15. A retention cuff according to claim 12, wherein the one or more side elements includes a plurality of spars connected to and extending in an axial direction from the annular cuff wall, and wherein distal ends of the one or more spars are joined to one another at a blunt nose axially aligned with but spaced from the central opening.

16. A retention cuff according to claim 15, wherein the inflationless cuff wall has a curved bowl or dish shape and wherein the one or more spars are joined to the annular cuff wall radially inward of the perimeter outer edge of the inflationless cuff wall.

* * * * *